United States Patent [19]

Zaugg et al.

[11] 4,172,943
[45] Oct. 30, 1979

[54] (8-SUBSTITUTED-10-HYDROXY-5,5-DIMETHYL-1,2,3,4-TETRAHYDRO-5H-(1)BENZOPYRANO(4,3-C)PYRIDIN-2-YL)ACETYL UREAS AND DERIVATIVES

[75] Inventors: Harold E. Zaugg, Lake Forest; Cheuk M. Lee, Libertyville, both of Ill.

[73] Assignee: Abbott Laboratories, North Chicago, Ill.

[21] Appl. No.: 930,944

[22] Filed: Aug. 4, 1978

Related U.S. Application Data

[63] Continuation-in-part of Ser. No. 760,887, Jan. 21, 1977, abandoned.

[51] Int. Cl.$^2$ .............................................. C07D 491/04
[52] U.S. Cl. ................................ 544/126; 260/244.4; 546/89
[58] Field of Search ................... 544/126; 260/293.58, 260/295 T, 244.4; 546/89

[56] References Cited

U.S. PATENT DOCUMENTS 3,522,260   7/1970   Shulgin ............................. 260/295 T

*Primary Examiner*—John M. Ford
*Assistant Examiner*—R. W. Ramsuer
*Attorney, Agent, or Firm*—Robert L. Niblack; Gildo E. Fato

[57] ABSTRACT

A compound of the formula

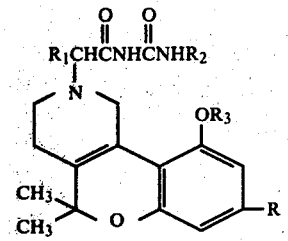

wherein $R_1$ is H or loweralkyl; $R_2$ is H, loweralkyl, phenyl or substituted phenyl; R is $C_3$-$C_{20}$ alkyl, phenyl alkyl or substituted phenyl alkyl; $R_3$ is H or

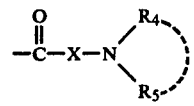

where X is a straight or branched chain alkylene group of 3 to 4 carbon atoms, and $R_4$ and $R_5$ are the same or different members of the group consisting of H or loweralkyl; or $R_4$ and $R_5$ taken together form a 6- or 6-member heterocyclic ring and containing no more than one additional heterocyclic atom, with or without α-loweralkyl substituents, and the acid addition salts thereof.

The compounds of this invention are useful as analgesics, tranquilizers, sedative-hypnotics and anti-glaucoma agents.

13 Claims, No Drawings

(8-SUBSTITUTED-10-HYDROXY-5,5-DIMETHYL-1,2,3,4-TETRAHYDRO-5H-(1)BENZOPYRANO(4,3-C)PYRIDIN-2-YL)ACETYL UREAS AND DERIVATIVES

This application is a continuation-in-part of application Ser. No. 760,887, filed Jan. 21, 1977, now abandoned.

SUMMARY OF THE INVENTION

The present invention relates to ureas and their derivatives, and more particularly to [8-substituted-10-hydroxy-5,5-dimethyl-1,2,3,4-tetrahydro-5H-[1]benzopyrano [4,3-c]pyridin-2-yl]acetyl ureas which are useful as analgesics, tranquilizers, sedative-hypnotics and antiglaucoma agents.

The present compounds are prepared by first alkylating an 8-substituted-10-hydroxy-5,5-dimethyl-1,2,3,4-tetrahydro-5H-[1]benzopyrano[4,3-c]pyridines with a haloacetylurea in the presence of an acid acceptor such as triethylamine in dimethylformamide. Then, these ureas are reacted with amino acids in the presence of dicyclohexylcarbodiimide in methylene chloride to provide the phenolic basic esters of this invention.

DETAILED DESCRIPTION OF THE INVENTION

This invention relates to ureas and their derivatives which are useful as analgesics, tranquilizers, sedative-hypnotics and antiglaucoma agents. The ureas are compounds falling within the following structural formula:

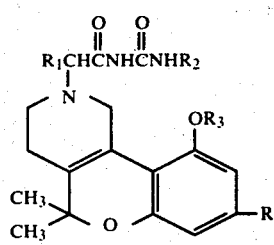

wherein $R_1$ is H or loweralkyl; $R_2$ is H, loweralkyl phenyl or substituted phenyl; R is $C_3$-$C_{20}$ alkyl, phenyl alkyl or substituted phenyl alkyl; $R_3$ is H or

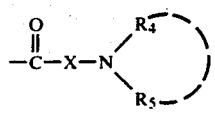

where X is a straight or branched chain alkylene group of 3 to 4 carbon atoms, and $R_4$ and $R_5$ are the same or different members of the group consisting of H or loweralkyl; or $R_4$ and $R_5$ taken together form a 6- or 7-membered heterocyclic ring and containing no more than one additional heterocyclic atom, with or without α-loweralkyl substituents, and the acid addition salts thereof.

The term "loweralkyl" refers to a $C_1$ to $C_6$ alkyl group including methyl, ethyl, n-propyl, iso-propyl, n-butyl, sec-butyl, tertiary-butyl, n-pentyl, iso-pentyl, neo-pentyl, n-hexyl and the like.

The term "$C_3$-$C_{20}$ alkyl" as used herein, refers to both straight and branched chain alkyl radicals including n-propyl, iso-propyl, n-butyl, sec-butyl, tertiary-butyl, n-pentyl, n-hexyl, 2-heptyl, n-heptyl, 3-methyl-2-octyl, 2-methyl-2-octyl, n-octyl, n-nonyl, 2-tetradecyl, 2-eicosanyl, and the like.

The term "phenyl alkyl" refers to a straight or branched alkyl group of 1 to 10 carbon atoms where one of the hydrogen atoms of the alkyl group is substituted by phenyl or a substituted phenyl.

"Substituted phenyl" as used herein refers to phenyl substituted by halo, such as chloro, bromo or fluorophenyl, or loweralkyl phenyl, such as methyl, ethyl, propyl or butyl phenyl.

The compounds of this invention exhibit activity as analgesics, tranquilizers, sedative-hypnotics and antiglaucoma agents. The analgesic activity is obtained at dosages of from 1 to 10 mg/kg of body weight orally and from 0.2 to 5.0 mg/kg of body weight interperitoneally (i.p.) Similarly, the tranquilizing activity is obtained at dosages of from 1.5 to 15.0 mg/kg of body weight orally and from 0.5 to 5.0 mg/kg of body weight interperitoneally (i.p.).

The present compounds may be prepared by means of a variety of techniques. For example, the compounds may be prepared by the alkylation of an 8-substituted-10-hydroxy-5,5-dimethyl-1,2,3,4-tetrahydro-5H-[1]benzopyrano[4,3-c]pyridine with a haloacetylurea and an acid acceptor such as triethylamine in dimethylformamide (DMF), as illustrated in Scheme I, below. The reaction of these ureas with amine-acids in the presence of dicyclohexylcarbodiimide (DCC) in methylene chloride provide the phenolic basic esters.

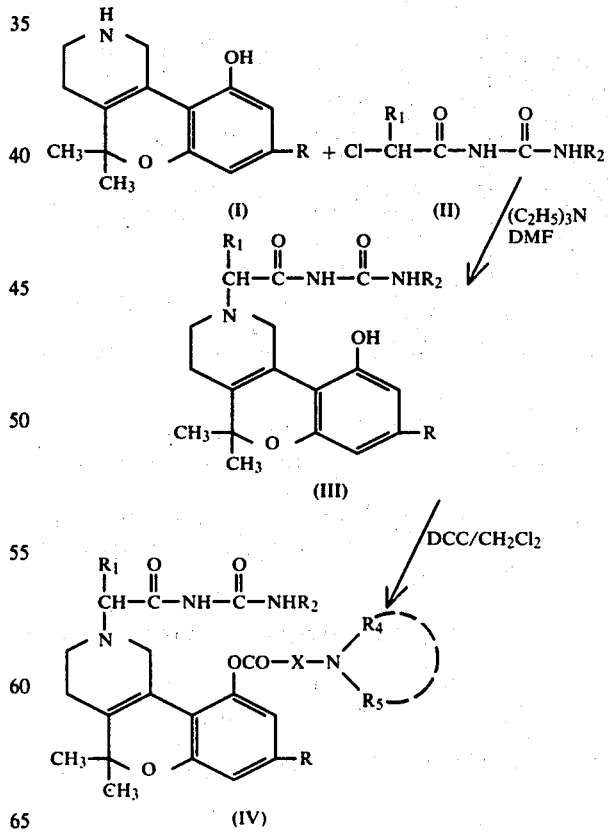

wherein $R_1$, $R_2$, $R_4$ and $R_5$ are as defined above and R is

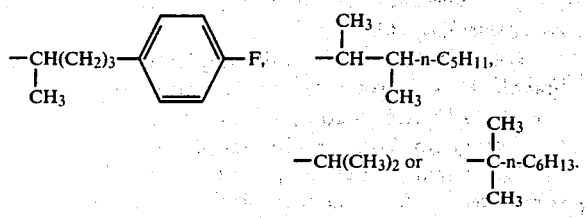

The starting compounds (I) may be selected from the following:

8-[5-(4-chlorophenyl)-2-pentyl]-10-hydroxy-5,5-dimethyl-1,2,3,4-tetrahydro-5H-[1]benzopyrano-[4,3-c]pyridine (R=5-(4-fluorophenyl)-2-pentyl);

8-[5-(4-bromophenyl)-2-pentyl]-10-hydroxy-5,5-dimethyl-1,2,3,4-tetrahydro-5H-[1]benzopyrano-[4,3-c]pyridine (R=5-(4-fluorophenyl)-2-pentyl);

8-[5-(4-fluorophenyl)-2-pentyl]-10-hydroxy-5,5-dimethyl-1,2,3,4-tetrahydro-5H-[1]benzopyrano-[4,3-c]pyridine (R=5-(4-fluorophenyl)-2-pentyl);

8-[5-(phenyl)-2-pentyl]-10-hydroxy-5,5-dimethyl-1,2,3,4-tetrahydro-5H-[1]benzopyrano-[4,3-c]pyridine (R=5-(4-fluorophenyl)-2-pentyl);

8-[5-(4-methylphenyl)-2-pentyl]-10-hydroxy-5,5-dimethyl-1,2,3,4-tetrahydro-5H-[1]benzopyrano-[4,3-c]pyridine (R=5-(4-fluorophenyl)-2-pentyl);

10-Hydroxy-5,5-dimethyl-8-(1,2-dimethylheptyl)-1,2,3,4-tetrahydro-5H-[1]benzopyrano[4,3-c]pyridine (R=1,2-dimethylheptyl);

10-Hydroxy-8-isopropyl-5,5-dimethyl-1,2,3,4-tetrahydro-5H-[1]benzopyrano[4,3-c]pyridine (R=isopropyl); and 10-Hydroxy-5,5-dimethyl-8-(1,1-dimethylheptyl)-1,2,3,4-tetrahydro-5H-[1]benzopyrano[4,3-c]pyridine (R=1,1-dimethylheptyl).

The compounds that may be produced according to the above illustrated method include:

V. {{8-[5-(4-chlorophenyl)-2-pentyl]-10-hydroxy-5,5-dimethyl-1,2,3,4-tetrahydro-5H-[1]benzopyrano-[4,3-c]pyridin-2-yl}acetyl}urea VI. {{8-[5-(4-bromophenyl)-2-pentyl]-10-hydroxy-5,5-dimethyl-1,2,3,4-tetrahydro-5H-[1]benzopyrano-[4,3-c]pyridin-2-yl}acetyl}urea VII. {{8-[5-(4-fluorophenyl)-2-pentyl]-10-hydroxy-5,5-dimethyl-1,2,3,4-tetrahydro-5H-[1]benzopyrano-[4,3-c]pyridin-2-yl}acetyl}urea VIII. {{8-[5-(phenyl)-2-pentyl]-10-hydroxy-5,5-dimethyl-1,2,3,4-tetrahydro-5H-[1]benzopyrano-[4,3-c]pyridin-2-yl}acetyl}urea IX. {{8-[5-(4-methylphenyl)-2-pentyl]-10-hydroxy-5,5-dimethyl-1,2,3,4-tetrahydro-5H-[1]benzopyrano-[4,3-c]pyridin-2-yl}acetyl}urea X. {[10-Hydroxy-5,5-dimethyl-8-(1,2-dimethylheptyl)-1,2,3,4-tetrahydro-5H-[1]benzopyrano[4,3-c]-pyridin-2-yl]acetyl}urea XI. [(10-Hydroxy-8-isopropyl-5,5-dimethyl-1,2,3,4-tetrahydro-5H-[1]benzopyrano[4,3-c]pyridin-2-yl)acetyl]urea XII. {[10-Hydroxy-5,5-dimethyl-8-(1,1-dimethylheptyl)-1,2,3,4-tetrahydro-5H-[1]benzopyrano[4,3-c]-pyridin-2-yl]acetyl}urea XIII. N-{[10-Hydroxy-5,5-dimethyl-8-(1,2-dimethylheptyl)-1,2,3,4-tetrahydro-5H-[1]benzopyrano[4,3-c]-pyridin-2-yl]acetyl}-N'-methylurea XIV. N-{[10-Hydroxy-5,5-dimethyl-8-(1,2-dimethylheptyl)-1,2,3,4-tetrahydro-5H-[1]benzopyrano[4,3-c]pyridin-2-yl]acetyl}-N'-phenylurea XV. {[10-Hydroxy-5,5-dimethyl-8-(1,2-dimethylheptyl)-1,2,3,4-tetrahydro-5H-[1]benzopyrano[4,3-c]-pyridin-2-yl]-α-methylacetyl}urea XVI. {{5,5-Dimethyl-8-(1,2-dimethylheptyl)-10-(4-piperidonobutyryloxy)-1,2,3,4-tetrahydro-5H-[1]benzopyrano[4,3-c]pyridin-2-yl}acetyl}urea hydrochloride XVII. {{5,5-Dimethyl-10-[4-(dimethylamino)-butyryloxy)]-8-(1,2-dimethylheptyl)-1,2,3,4-tetrahydro-5H-[1]benzopyrano[4,3-c]pyridin-2-yl}acetyl}urea hydrochloride XVIII. {{8-[5-(4-Fluorophenyl)-2-pentyl]-5,5-dimethyl-10-(4-morpholinobutyryloxy)-1,2,3,4-tetrahydro-5H-[1]benzopyrano[4,3-c]pyridin-2-yl}acetyl}urea hydrochloride IX. {[10-(4-Homopipidinobutyryloxy)-5,5-dimethyl-8-(1,1-dimethylheptyl)-1,2,3,4-tetrahydro-5H-[1]benzopyrano[4,3-c]pyridin-2-yl]acetyl}urea hydroxhloride XX. {{5,5-Dimethyl-8-(1,2-dimethylheptyl)-10-[4-(2-methylpiperidino)-2-methylbutyryloxy]-1,2,3,4-tetrahydro-5H-[1]benzopyrano[4,3-c]pyridin-2-yl}acetyl}urea hydrochloride The following examples are presented to further illustrate the invention.

EXAMPLE 1

{{8-[5-(4-Fluorophenyl)-2-pentyl]-10-hydroxy-5,5-dimethyl-1,2,3,4-tetrahydro-5H-[1]benzopyrano[4,3-c]pyridin-2-yl}acetyl}urea (V)

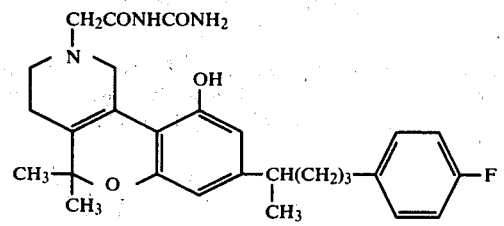

A solution of 1.50 g. (0.011 mole) of chloroacetyl urea in 20 ml. of dimethylformamide was added dropwise to a stirred solution of 3.95 g. (0.01 mole) of 8-[5-(4-fluorophenyl)-2-pentyl]-10-hydroxy-5,5-dimethyl-1,2,3,4-tetrahydro-5H-[1]benzopyrano[4,3-c]pyridine in 25 ml. of dimethylformamide and 1.11 g. (0.011 mole) of triethylamine. After stirring at room temperature for 22 hours, the mixture was diluted with 45 ml. of water and extracted with ether. The combined ether extracts were washed with water, dried over anhydrous sodium sulfate, and evaporated in vacuo. The residue was recrystallized from acetonitrile, m.p. 133°–134°.

Analysis Calcd. for $C_{28}H_{34}FN_3O_4$: C, 67.86; H, 6.92; N, 8.48. Found: C, 67.52; H, 7.12; N, 8.38.

EXAMPLE 2

{[10-Hydroxy-5,5-dimethyl-8-(1,2-dimethylheptyl)-1,2,3,4-tetrahydro-5H-[1]benzopyrano[4,3-c]pyridin-2-yl]acetyl}urea (VI)

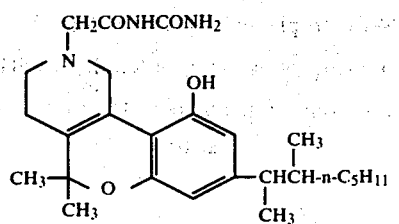

A solution of 1.50 g. (0.011 mole) of chloroacetylurea in 25 ml. of dimethylformamide was added dropwise to a stirred solution of 3.57 g. (0.01 mole) of 10-hydroxy-5,5-dimethyl-8-(1,2-dimethylheptyl)-1,2,3,4-tetrahydro-5H-[1]benzopyrano[4,3-c]pyridine in 20 ml. of dimethylformamide and 1.11 g. (0.011 mole) of triethylamine. After stirring for 24 hours, 65 ml. of water was added dropwise to the stirred mixture. The solid was filtered and recrystallized from acetonitrile, m.p. 131°–133°.

Analysis Calcd. for $C_{26}H_{39}N_3O_4$: C, 68.24; H, 8.59; N, 9.18. Found: C, 67.94; H, 8.66; N, 9.17.

EXAMPLE 3

[(10-Hydroxy-8-isopropyl-5,5-dimethyl-1,2,3,4-tetrahydro-5H-[1]benzopyrano[4,3-c]pyridin-2-yl)acetyl]urea (VII)

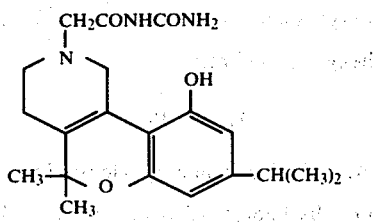

The above-titled compound was prepared by reacting 10-hydroxy-8-isopropyl-5,5-dimethyl-1,2,3,4-tetrahydro-5H-[1]benzopyrano[4,3-c]pyridine with chloroacetylurea according to the method of Example 2; m.p. 164°–166°.

Analysis Calcd. for $C_{20}H_{27}N_3O_4$: C, 64.32; H, 7.29; N, 11.25. Found: C, 64.60; H, 7.26; N, 11.27.

EXAMPLE 4

{[10-Hydroxy-5,5-dimethyl-8-(1,1-dimethylheptyl)-1,2,3,4-tetrahydro-5H-[1]benzopyrano[4,3-c]pyridin-2-yl]acetyl}urea (VIII)

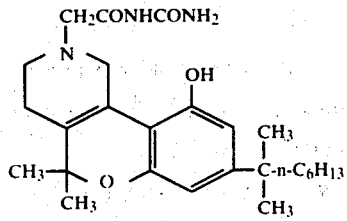

The above-titled compound was prepared by reacting 10-hydroxy-5,5-dimethyl-8-(1,1-dimethylheptyl)-1,2,3,4-tetrahydro-5H-[1]benzopyrano[4,3-c]pyridine with chloroacetyl-urea according to the method of Example 2.

EXAMPLE 5

N-{[10-Hydroxy-5,5-dimethyl-8-(1,2-dimethylheptyl)-1,2,3,4-tetrahydro-5H-[1]benzopyrano[4,3-c]pyridin-2-yl]acetyl}-N'-methylurea (IX)

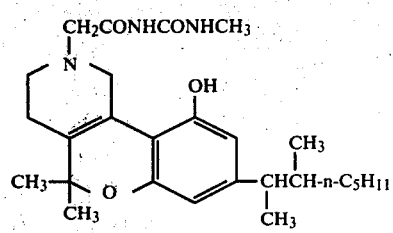

The above-titled compound was prepared by reacting 10-hydroxy-5,5-dimethyl-8-(1,2-dimethylheptyl)-1,2,3,4-tetrahydro-5H-[1]benzopyrano[4,3-c]pyridine with N-chloroacetyl-N'-methylurea according to the method of Example 2; m.p. 145°–147°.

Analysis Calcd. for $C_{27}H_{41}N_3O_4$: C, 68.76; H, 8.76; N, 8.91. Found: C, 69.20; H, 9.01; N, 8.93.

EXAMPLE 6

N-{[10-Hydroxy-5,5-dimethyl-8-(1,2-dimethylheptyl)-1,2,3,4-tetrahydro-5H-[1]benzopyrano[4,3-c]pyridin-2-yl]acetyl}-N'-phenylurea (X)

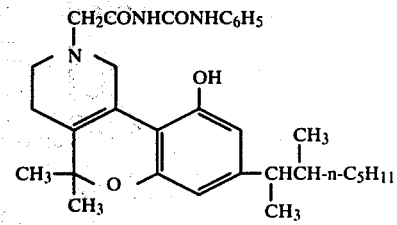

The above-titled compound was prepared by reacting 10-hydroxy-5,5-dimethyl-8-(1,2-dimethylheptyl)-1,2,3,4-tetrahydro-5H-[1]benzopyrano[4,3-c]pyridine with N-chloroacetyl-N'-phenylurea according to the method of Example 1; m.p. 159°–161°.

Analysis Calcd. for $C_{32}H_{43}N_3O_4$: C, 72.01; H, 8.12; N, 7.87. Found: C, 71.62; H, 8.15; N, 7.88.

EXAMPLE 7

{[10-Hydroxy-5,5-dimethyl-8-(1,2-dimethylheptyl)-1,2,3,4-tetrahydro-5H-[1]benzopyrano[4,3-c]pyridin-2-yl]-α-methylacetyl}urea (XI)

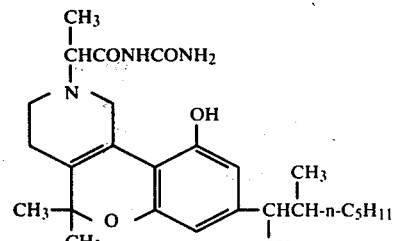

A solution of 1.66 g. (0.011 mole) of 2-chloropropionylurea in 20 ml. of dimethylformamide was added dropwise to a stirred solution of 3.57 g. (0.01 mole) of 10-hydroxy-5,5-dimethyl-8-(1,2-dimethylheptyl)-1,2,3,4-tetrahydro-5H-[1]benzopyrano[4,3-c]pyridine in 20 ml. of dimethylformamide and 1.11 g. (0.011 mole) of triethylamine. The reaction mixture was stirred at room temperature for 72 hours, diluted with 60 ml. of water, and extracted with ether. The ether extracts were washed with water, dried over anhydrous sodium sulfate, and evaporated in vacuo. The residue was purified by chromatography on a 100–200 mesh Florisil activated magnesium silicate column and chloroform; m.p. 95°–100°.

Analysis Calcd. for $C_{27}H_{41}N_3O_4$: C, 68.76; H, 8.76; N, 8.91. Found: C, 68.78; H, 8.93; N, 8.54.

EXAMPLE 8

{[5,5-Dimethyl-8-(1,2-dimethylheptyl)-10-(4-piperidinobutyryloxy)-1,2,3,4-tetrahydro-5H-[1]benzopyrano[4,3-c]pyridin-2-yl]acetyl}urea hydrochloride
(XII)

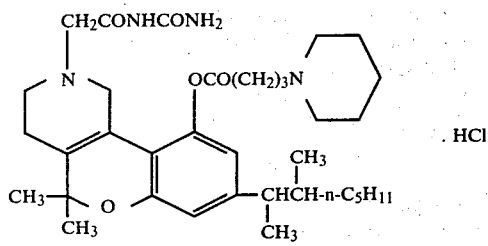

A mixture of 1.14 g. (0.0025 mole) of {[10-hydroxy-5,5-dimethyl-8-(1,2-dimethylheptyl)-1,2,3,4-tetrahydro-5H-[1]benzopyrano[4,3-c]pyridin-2-yl]acetyl}urea, 0.52 g. (0.0025 mole) of 4-piperidinobutyric acid hydrochloride, 0.54 g. (0.0026 mole) of dicyclohexylcarbodiimide, and 170 ml. of dried methylene chloride was stirred at room temperature for 26 hours. The reaction mixture was cooled at approximately 6° C. overnight and was filtered to remove dicyclohexylurea. The filtrate was evaporated in vacuo and the residue was dissolved in 3 ml. of methylene chloride and 12.5 ml. of cyclohexane. After standing overnight in the cold room (approximately 6° C.), the solid was filtered and recrystallized from methylene chloride-ether, giving 1.1 g. of the product, m.p. 167°–170°.

Analysis Calcd. for $C_{35}H_{54}N_4O_5 \cdot HCl$: C, 64.94; H, 8.57; N, 8.66. Found: C, 64.84; H, 8.60; N, 8.59.

EXAMPLE 9

{[5,5-Dimethyl-10-[4-(dimethylamino)butyryloxy]-8-(1,2-dimethylheptyl)-1,2,3,4-tetrahydro-5H-[1]benzopyrano[4,3-c]pyridin-2-yl]acetyl}urea hydrochloride
(XIII)

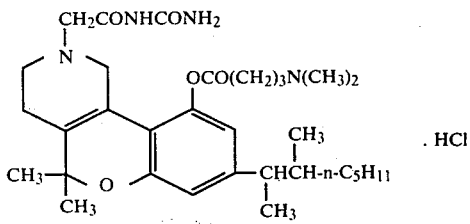

The above-titled compound was prepared according to the method of Example 8 by reacting equimolar quantities of {[10-hydroxy-5,5-dimethyl-8-(1,2-dimethylheptyl)-1,2,3,4-tetrahydro-5H-[1]benzopyrano[4,3-c]pyridin-2-yl]acetyl}urea and 4-(dimethylamino)butyric acid hydrochloride in the presence of dicyclohexylcarbodiimide.

EXAMPLE 10

{{8-[5-(4-Fluorophenyl)-2-pentyl]-5,5-dimethyl-10-(4-morpholinobutyryloxy)-1,2,3,4-tetrahydro-5H-[1]benzopyrano[4,3-c]pyridin-2-yl}acetyl}urea hydrochloride
(XIV)

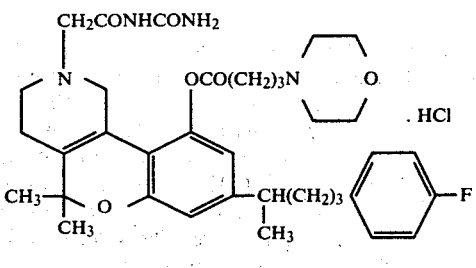

The above-titled compound was prepared according to the method of Example 8 by reacting equimolar quantities of {{8-[5-(4-fluorophenyl)-2-pentyl]-10-hydroxy-5,5-dimethyl-1,2,3,4-tetrahydro-5H-[1]benzopyrano[4,3-c]pyridin-2-yl}acetyl}urea and 4-morpholinobutyric acid hydrochloride in the presence of dicyclohexylcarbodiimide.

EXAMPLE 11

{[10-(4-Homopiperidinobutyryloxy)-5,5-dimethyl-8-(1,1-dimethylheptyl)-1,2,3,4-tetrahydro-5H-[1]benzopyrano[4,3-c]pyridin-2-yl]acetyl}urea hydrochloride
(XV)

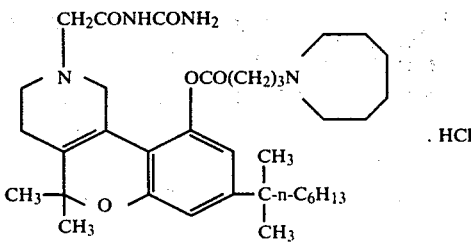

The above-titled compound was prepared according to the method of Example 8 by reacting equimolar quantities of [10-hydroxy-5,5-dimethyl-8-(1,1-dimethylheptyl)-1,2,3,4-tetrahydro-5H-[1]benzopyrano[4,3-c]pyridin-2-yl)acetyl]urea and 4-homopiperidinobutyric acid hydrochloride in the presence of dicyclohexylcarbodiimide.

EXAMPLE 12

{{5,5-Dimethyl-8-(1,2-dimethylheptyl)-10-[4-(2-methylpiperidino)-2-methylbutyryloxy]-1,2,3,4-tetrahydro-5H-[1]benzopyrano[4,3-c]pyridin-2-yl}-acetyl}urea hydrochloride (XVI)

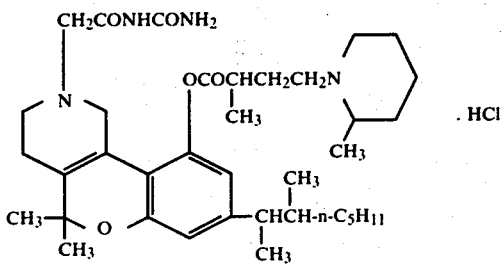

The above-titled compound was prepared according to the method of Example 8 by reacting equimolar quantities of {[10-hydroxy-5,5-dimethyl-8-(1,2-dimethylheptyl)-1,2,3,4-tetrahydro-5H-[1]benzopyrano[4,3-c]pyridin-2-yl]acetyl}urea and [4-(2-methylpiperidino)]-2-methylbutyric acid hydrochloride in the presence of dicyclohexylcarbodiimide.

TEST II

Rat Tail Flick Test

In this test, groups of 10 male, Sprague-Dawley rats, weighing 142–170 g. were orally (p.o.) gavaged with compound (V) after the average normal response time to radiated heat focused on the tail had been established by two trials. Response times were recorded hourly for 3 hours after the administration of the compound. The activity was determined as the percent increase in response time over the average normal response for the response for the respective group. The results of the test are provided in the table below. An $ED_{50}$ value representing the dose producing a 50% increase in average response time was calculated by a linear regression program.

| Effect of Compound V in the Rat Tail Flick test | | | | | |
|---|---|---|---|---|---|
| Compound (V) mg./kg., p.o. | Normal | 1 Hr. | 2 Hrs. | 3 Hrs. | Activity-Increase in Response Time (2 Hrs.) |
| 1.0 | 8.03 | 9.03 | 10.44 | 11.22 | 30.0% |
| 2.0 | 6.80 | 8.92 | 10.61 | 10.99 | 56.0% |
| 4.0 | 8.30 | 11.13 | 16.20 | 16.98[a] | 95.2% |
| 8.0 | 7.97 | 13.63[a] | 15.83[a] | 14.32 | 98.6% |

[a]Averages include maximum values (30 seconds cut-off time). $ED_{50}$ (2 Hrs.) = 1.6 mg./kg. (0.02, 3.19)

EXAMPLE 13

Pharmacological Tests

There were several tests carried out with compound (V), and the results of the tests are provided below.

TEST I

Mouse Writhing Test

In this test, groups of 5 female, ICR mice (Schmidt) weighing 19–25 g. were orally (p.o.) gavaged with compound (V) one hour prior to the intraperitoneal injection of 0.4 ml. of acetic acid 0.5% (v/v). Five minutes after the acid injection, the number of writhing responses over a 20 minute period were counted. One group received an oral dose of vehicle only to serve as controls. Activity was determined as the percent difference (inhibition) between the average number of writhes for the test groups as compared to the controls. The results of the tests are provided in the table below. An $ED_{50}$ value representing the dose producing a 50% inhibition of the writhing response was calculated by a linear regression program.

| Effect of Compound V in the Mouse Acetic Acid Writhing Test | | |
|---|---|---|
| Group Treatment mg./kg., p.o. | Ave. Number of Writhes (20 min.) | Activity % Inhibition |
| Controls[a] | 55.0 | — |
| 0.5 | 28.4 | 48.4 |
| 1.0 | 27.4 | 50.2 |
| 2.0 | 15.2 | 72.4 |
| 4.0 | 6.0 | 89.1 |

[a]0.5% methylcellulose:20 ml./kg.
$ED_{50}$ = 0.7 mg./kg. (0.4, 1.0)

TEST III

Rat Desoxyn Antagonism Test

In this test, the antagonism or potentiation of methamphetamine-induced hyperactivity in rats was evaluated in motor activity chambers equipped with photocells (Lehigh Valley, Model #1497). Groups of rats were premedicated with Compound (V) and then administered methamphetamine (1 mg./kg., i.p.). One rat was placed in each chamber and three rats were used per test dose. Effect was recorded as percent change in counts from the photocells compared to methamphetamine-treated controls. The test results are provided below.

| Antagonism Effect of Compound (V) | |
|---|---|
| Oral Dose mg./kg. | % Decreased Activity Over Control |
| 5 | 75 |
| 20 | 93 |
| 80 | 84 |

We claim:
1. A compound represented by the formula

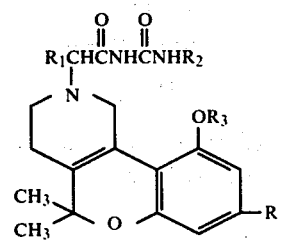

wherein $R_1$ is H or loweralkyl; $R_2$ is H, loweralkyl phenyl or phenyl substituted by halo or lower alkyl; R is $C_3$-$C_{20}$ alkyl, phenyl alkyl or halo or lower alkyl substituted phenyl wherein alkyl contains from 1 to 10 carbon atoms; $R_3$ is H or

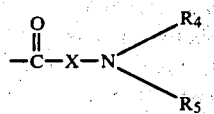

where X is a straight or branched chain alkylene group of 3 to 4 carbon atoms, and R$_4$ and R$_5$ are the same or different members of the group consisting of H or loweralkyl; or R$_4$ and R$_5$ taken together form a piperidino, morpholino or homopiperidino ring with or without α-loweralkyl substituents, and the acid addition salts thereof.

2. A compound according to claim 1 wherein R$_1$ is H, R$_2$ is H, R$_3$ is H and R is

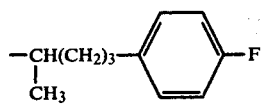

3. A compound according to claim 1 wherein R$_1$ is H, R$_2$ is H, R$_3$ is H and R is

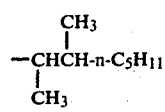

4. A compound according to claim 1 wherein R$_1$ is H, R$_2$ is H, R$_3$ is H and R is

—CH(CH$_3$)$_2$

5. A compound according to claim 1 wherein R$_1$ is H, R$_2$ is H, R$_3$ is H and R is

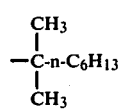

6. A compound according to claim 1 wherein R$_1$ is H, R$_2$ is CH$_3$, R$_3$ is H and R is

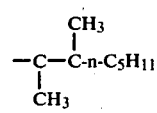

7. A compound according to claim 1 wherein R$_1$ is H, R$_2$ is C$_6$H$_5$, R$_3$ is H and R is

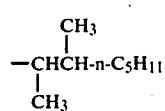

8. A compound according to claim 1 wherein R$_1$ is CH$_3$, R$_2$ is H, R$_3$ is H and R is

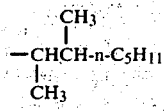

9. A compound according to claim 1 wherein R$_1$ is H, R$_2$ is H, R$_3$ is

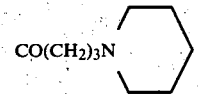

and R is

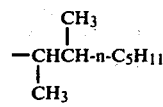

10. A compound according to claim 1 wherein R$_1$ is H, R$_2$ is H, R$_3$ is CO(CH$_2$)$_3$N(CH$_3$)$_2$ and R is

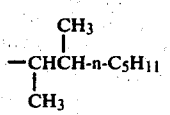

11. A compound according to claim 1 wherein R$_1$ is H, R$_2$ is H, R$_3$ is

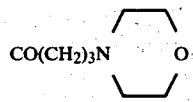

and R is

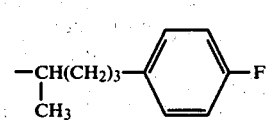

12. A compound according to claim 1 wherein R$_1$ is H, R$_2$ is H, R$_3$ is

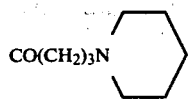

and R is

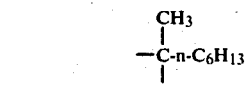

13. A compound according to claim 1 wherein R$_1$ is H, R$_2$ is H, R$_3$ is

and R is

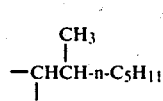

* * * * *

UNITED STATES PATENT AND TRADEMARK OFFICE
CERTIFICATE OF CORRECTION

PATENT NO. : 4,172,943
DATED : October 30, 1979
INVENTOR(S) : Harold E. Zaugg, et. al.

It is certified that error appears in the above—identified patent and that said Letters Patent are hereby corrected as shown below:

In column 11, lines 1-5,

" 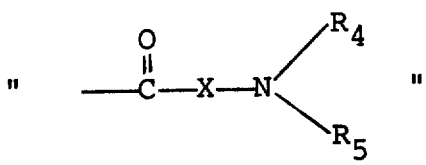 "

should read

" 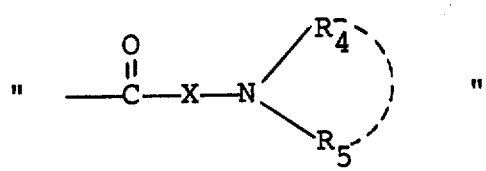 "

Signed and Sealed this

Seventh Day of April 1981

[SEAL]

Attest:

RENE D. TEGTMEYER

Attesting Officer     Acting Commissioner of Patents and Trademarks